(12) United States Patent
Klingenbeck et al.

(10) Patent No.: US 9,057,759 B2
(45) Date of Patent: Jun. 16, 2015

(54) METHOD FOR POSITIONING THE FOCUS OF A GRADIENT FIELD AND TREATMENT FACILITY

(75) Inventors: Klaus Klingenbeck, Aufseβ (DE); Michael Maschke, Lonnerstadt (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 604 days.

(21) Appl. No.: 13/104,271

(22) Filed: May 10, 2011

(65) Prior Publication Data

US 2011/0282184 A1  Nov. 17, 2011

(30) Foreign Application Priority Data

May 12, 2010  (DE) .......................... 10 2010 020 350

(51) Int. Cl.
| | | |
|---|---|---|
| A61N 2/00 | (2006.01) | |
| G01R 33/28 | (2006.01) | |
| G01R 33/48 | (2006.01) | |
| A61B 5/055 | (2006.01) | |
| A61B 6/12 | (2006.01) | |

(Continued)

(52) U.S. Cl.
CPC .............. *G01R 33/287* (2013.01); *A61B 5/055* (2013.01); *A61B 6/12* (2013.01); *A61B 2019/2253* (2013.01); *A61B 2019/5236* (2013.01); *A61B 2019/5238* (2013.01); *A61B 2019/5251* (2013.01); *A61B 2019/5263* (2013.01); *A61B 2019/5289* (2013.01); *A61K 9/0009* (2013.01); *G01R 33/4812* (2013.01)

(58) Field of Classification Search
CPC .............. A61B 2019/2253; A61B 2019/5236; A61B 2019/5238; A61B 2019/5251; A61B 2019/5263; A61B 2019/5289; A61B 5/055; A61B 6/12; A61K 9/0009; G01R 33/287; G01R 33/4812
See application file for complete search history.

(56) References Cited

U.S. PATENT DOCUMENTS

| | | | | |
|---|---|---|---|---|
| 5,488,951 | A | * | 2/1996 | Bauer et al. .................... 600/427 |
| 6,273,858 | B1 | * | 8/2001 | Fox et al. ....................... 600/466 |
| 6,514,481 | B1 | | 2/2003 | Prasad et al. |

(Continued)

FOREIGN PATENT DOCUMENTS

| | | |
|---|---|---|
| DE | 102006060421 A1 | 6/2008 |
| DE | 102007028777 A1 | 12/2008 |

(Continued)

OTHER PUBLICATIONS

Liu et al., "Radiofrequency Tumor Ablation: Insight into Improved Efficacy Using Computer Modeling", AJR: 184, Apr. 2005, pp. 1347-1352.

(Continued)

*Primary Examiner* — Ruth S Smith

(57) ABSTRACT

A method for guiding nanoparticles to a target location by a magnetic gradient field and/or holding them at the target location is proposed. The magnetic gradient field is generated by a magnet system with at least one magnet. A focus of the magnet system is registered with an X-ray device. At least one three-dimensional image dataset showing the target location is captured by the X-ray device. The position of the target location is determined manually and/or automatically in the image dataset or in an image dataset determined therefrom and is positioned automatically based on the registration of the focus so that the focus coincides with the position of the target location.

19 Claims, 6 Drawing Sheets

(51) Int. Cl.
*A61B 19/00* (2006.01)
*A61K 9/00* (2006.01)

(56) References Cited

U.S. PATENT DOCUMENTS

| | | | |
|---|---|---|---|
| 6,600,319 B2 | 7/2003 | Golan | |
| 7,216,383 B2 | 5/2007 | Heinl | |
| 8,251,885 B2* | 8/2012 | Ueda et al. | 600/12 |
| 8,364,245 B2* | 1/2013 | Kruecker | 600/426 |
| 2004/0064153 A1* | 4/2004 | Creighton et al. | 607/1 |
| 2004/0076582 A1 | 4/2004 | Dimatteo et al. | |
| 2005/0060804 A1 | 3/2005 | Heinl et al. | |
| 2005/0075563 A1* | 4/2005 | Sukovic et al. | 600/427 |
| 2006/0120507 A1 | 6/2006 | Brunner et al. | |
| 2006/0269479 A1* | 11/2006 | Colton et al. | 424/1.69 |
| 2007/0025524 A1* | 2/2007 | Yue | 378/205 |
| 2007/0041497 A1* | 2/2007 | Schnarr et al. | 378/65 |
| 2008/0199400 A1* | 8/2008 | Dyer et al. | 424/9.1 |
| 2009/0022383 A1* | 1/2009 | Falco et al. | 382/131 |
| 2009/0082784 A1* | 3/2009 | Meissner et al. | 606/130 |
| 2010/0066363 A1 | 3/2010 | Brazdeikis et al. | |
| 2010/0114308 A1 | 5/2010 | Maschke | |
| 2010/0204674 A1 | 8/2010 | Forbes et al. | |
| 2010/0266220 A1* | 10/2010 | Zagorchev et al. | 382/285 |
| 2010/0284601 A1* | 11/2010 | Rubner et al. | 382/132 |
| 2011/0306870 A1* | 12/2011 | Kuhn | 600/411 |
| 2011/0313689 A1* | 12/2011 | Holley et al. | 702/56 |
| 2012/0035462 A1* | 2/2012 | Maurer et al. | 600/411 |

FOREIGN PATENT DOCUMENTS

| | | |
|---|---|---|
| DE | 102008049771 A1 | 4/2010 |
| WO | WO 2009000478 A1 | 12/2008 |

OTHER PUBLICATIONS

Meyer et al., "The value of combined soft-tissue and vessel visualisation before transarterial chemoembolisation of the liver using C-arm computed tomography", European Society of Radiology 2009, Published online: May 8, 2009; pp. 1-8.

Angio-MR MIYabi: The smart link between Artis zee and MAGNETOM TIM, Siemens AG, Medical Solutions, Apr. 2008, Order No. A91AX-20805-11T1-7600; pp. 1-8.

A confident investment, syngo DynaCT liver tumor treatment, Siemens AG, Medical Solutions, Nov. 2008, Order No. A91AX-20824-11C1-7600; pp. 1-12.

Alexiou, Christoph et al, "Magnetic Drug Targeting" Section for Experimental Oncology and Nanomedicine, Workshop Cluster of Excellence Competition-Let's share the opportunity! Jul. 9, 2009, 6pm IZMP Erlangen.

* cited by examiner

METHOD FOR POSITIONING THE FOCUS OF A GRADIENT FIELD AND TREATMENT FACILITY

CROSS REFERENCE TO RELATED APPLICATIONS

This application claims priority of German application No. 10 2010 020 350.5 filed May 12, 2010, which is incorporated by reference herein in its entirety.

FIELD OF THE INVENTION

The invention relates to a method for positioning of the focus of a magnetic gradient field generated by a magnet system with at least one magnet guiding nanoparticles to a target location and/or keeping them there, as well as to an associated treatment facility.

BACKGROUND OF THE INVENTION

Cancers have long represented a challenge to modem medicine. Classical cancer therapy can generally provide the following measures:
1. Surgical removal of the tumor
2. Chemotherapy
3. Radiotherapy
4. A combination of the three above measures.

Despite all the advances in the measures listed above, tumors or metastases can recur in many patients. Depending on the state of health of the patient, their age and the type of tumor, the forms of therapy described above can be repeated. However it can also occur that a patient is "therapied out", meaning that the above-mentioned classical therapy measures can no longer be employed, since the patient can no longer endure the stress of these therapies physically and/or mentally.

For such "therapied out" patients the practice of applying strong painkillers is known, some of which can also be introduced directly via a catheter into the tumor area. In such cases however this only fights the pain, no healing is achieved.

Thus in recent times so-called tumor ablation has been recommended as a new method of treatment. This makes provision for guiding a tool, for example a catheter or a biopsy needle, to the tumor or the metastasis and damaging the tumor with the aid of various forms of energy or by injection of alcohol.

What is referred to as thermoablation will be described here in greater detail by way of example. Radio frequency (RF), microwave, ultrasound and/or laser energy is used for thermoablation. In such cases the tumor cells are killed by high temperatures, while healthy tissue remains protected. In radio frequency ablation (RFA) an interventional radiologist, with the aid of imaging technologies, introduces a thin needle into the patient's tumor. Radiofrequency energy is transferred from the tip of the needle to the target tissue, where it generates great heat and thereby kills the tumor. The dead tissue shrinks and slowly forms a scar.

Depending on the size of the tumor, RFA can cause it to shrink or can kill it, whereby the life of a patient can be extended and their quality of life significantly improved. Since RFA involves a local method which has little or no adverse effect on healthy tissue, the treatment can be repeated frequently.

Pain caused by tumors and also other symptoms of weakness are mitigated by the size of the tumor being reduced or by new tumors which occur being treated. Although the tumors themselves often cause no pain, they can press on nerves or vital organs, which causes great pain under some circumstances. RFA can be employed for small to medium-size tumors, cf. the article by Zhengium Liu entitled "Radiofrequency tumor ablation", AJR: 184, April 2005, 1347 to 1352.

A great disadvantage of the above ablation therapy is that this can only be used with relatively small tumors. A very high proportion of tumors is discovered at a relatively late stage however and can thus no longer be treated by this form of therapy.

An alternative to ablation is so-called radio embolization, also called selective internal radiotherapy (SIRT). In such cases the vessels are sealed off with radioactive microcapsules, frequently having a spherical shape. These tiny spheres have an approximate diameter of five red blood corpuscles and attach themselves to the blood vessels of the tumor, from where they emit radiation which damages and especially kills the tumor cells.

The radioisotope Yttrium-90 is frequently used, with the microcapsules containing the radioisotope being produced immediately before the intervention and brought to the treatment clinic. Yttrium-90 is used by preference since it involves a pure Beta radiator. Thus the undesired radiation exposure for persons in the immediate environment is low and 90% of the energy of the particle radiation is deposited in the tissue within a radius of approx. 9 to 11 mm. The comparatively short physical half-life only requires a short stay in the nuclear medical clinic, for example of around 48 hours.

The production of such radioactive therapeutic agents or of corresponding microcapsules is described in US 2004/0076582 for example.

Radioembolization is carried out as a visually-controlled therapy by an interventional radiologist in collaboration with a nuclear medical expert. After a local anesthetic a thin catheter is introduced into the artery via a small skin puncture in the strip. This catheter is then moved under flouroscopy control to the target location, i.e. the tumor. For the treatment of a liver tumor the catheter can be guided under fluoroscopy control along the liver artery (Arteria Hepatica). The radioactive isotope is injected through the catheter in the form of microcapsules, especially microspheres, directly into those artery branches which supply the tumor, especially the liver tumor. These microspheres remain lodged in the tumor vessels where they emit their tumor-killing radiation. This radiation is restricted to this area, its dose can be correspondingly higher without any collateral damage being caused to healthy tissue during the treatment.

Radio embolization generally involves a palliative treatment method, which means that it does not heal the cancer. Despite this patients profit greatly from this method since their life expectancy is increased by it and their quality of life is improved. The therapy approach involved is a relatively new one but it has already shown successes in the treatment of primary tumors or metastases. To date fewer side-effects have been identified with this treatment method than for example with typical chemotherapies.

Radio embolization is used for example in hepatocellular carcinomas (HCC), for cholangiocellular carcinomas and with liver metastases such as of intestinal and breast cancer or of other malignomas. The most frequent side-effects which occur are tiredness, which can last for seven to ten days.

A disadvantage of this method is that, if the radioactive microcapsules find their way into the lungs, gall bladder or stomach, they can cause radiation damage there.

A further new very promising treatment method is so-called "magnetic drug targeting" in which chemotherapeutic-laden magnetic nanoparticles are introduced into the tumor via a catheter or a puncturing needle. Subsequently the magnetic nanoparticles are concentrated by a magnet in the area of the greatest field gradient and then release the chemotherapeutic medicament in the tumor. Magnetic nanoparticles for therapy purposes are known for example from U.S. Pat. No. 6,514,481 B1.

The microcapsules or microspheres currently used mostly consist of a magnetic core, namely the magnetic nanoparticle, onto which the chemotherapeutics which lead to the destruction of the tumor cells are coated as an envelope.

As already indicated, these nanoparticles can be guided by magnetic fields in the room to a specific target location or held there, i.e. in the tumor volume for example, in order to act locally and selectively. In order to exert such magnetic holding forces inhomogeneous magnetic fields, especially with strong gradients (gradient field) are required which can be generated for example by an electromagnet but also by permanent magnets.

The magnetic gradient field is designed in such cases so that a spatial region, the so-called focus, exists within which the generated holding forces are at their maximum. In such cases it is frequently difficult to get this focus to cover the target location, with this operation currently frequently being performed manually on the basis of visual information or suchlike, which involves the risk of the treatments not having an effect or not having a sufficient effect at the target location. The positioning is then based on a purely optical estimation by the doctor, whereby a concentration at the incorrect point means that healthy sections of tissue can be damaged or thromboses can be created by accumulation of the microcapsules at the incorrect point.

SUMMARY OF THE INVENTION

Consequently the object of the invention is to specify a positioning method which allows an improved positioning.

To achieve this object in the method of the type stated at the start there is inventive provision for the magnet system to be registered with an X-ray device, with at least one image dataset showing the target location being captured by means of the X-ray device, the position of the target location being determined manually and/or automatically in the image dataset or from an image dataset derived therefrom and being positioned automatically taking into account the registration of the focus so that it coincides with the position of the target location.

Inventively it is thus proposed that an X-ray device be used which is registered with the magnet system or is at least able to be registered with it. Once a registration is namely produced, if the target location, i.e. especially the tumor, has been localized in three dimensions in the coordinate system of the X-ray device, a position in the coordinate system of the magnet system will also be determined which is to be taken in by the focus so that the target location can be automatically moved to by the magnet system. In concrete terms this means that the relative position of focus and target location is able to be changed by means of different adjustment means which allow a mechanical and/or electrical movement. Control parameters are determined automatically for these adjustment means so that the adjustment means is controlled accordingly, for example by a control device. This is all possible because of the registration.

The X-ray device, for example an X-ray device comprising a C-arm, especially with a flat panel detector, further allows access to the patient since the injection of the magnetic nanoparticles will be undertaken in the same room. By means of a biplanar system or by capturing consecutive pictures over time while adjusting the C-arm, X-ray pictures can be captured from which a three-dimensional position of the tumor can be deduced. However computed tomography-like methods are best suited for capturing the image dataset, for example the so-called dynaCT method, which is described for example by US 2006/0120507 A1.

There are basically two options for determining the position of the target location from the image dataset or from the image dataset derived from the captured image dataset. On the one hand there can be provision for the image dataset to be displayed typically in a plan view so that a user, for example a doctor, can identify the target location, especially the tumor, in the plan view and the position is thus able to be determined. A suitable display facility can be provided for this purpose. It should be pointed out even at this point that further parameters concerning the intervention can also be determined and if necessary set in such a plan view, for example in relation to the number of microcapsules needed or the like. Naturally it is also conceivable to have the target location in the image dataset localized automatically using automatic picture analysis, for example using suitable segmentation or edge-detection algorithms. Semi-automatic position determination is also conceivable in which a user for example specifies rough positioning, with the precise determination being carried out automatically for example by a control device.

It should also be pointed out at this juncture that the geometrical location of the field focus in the room can typically already be determined by the geometry of the at least one magnet, if necessary additionally by the use of electromagnets from the excitation currents. For example, a magnetic field map can also be stored in the control device for different settings of the adjustment means of the magnet system.

Consequently in the inventive method the focus can be brought largely automatically with high accuracy into alignment with the position of the tumor or of the target location. Thus the nanoparticles, especially the microcapsules containing them are optimally concentrated locally in the tumor and destroy the tumor with minimal side effects on surrounding healthy tissue. Consequently a generally higher precision and effectiveness of the treatment is made possible.

To achieve a basically available registration there can be provision for the magnet system or its components to have a fixed mechanical connection to the X-ray device. Alternately it is however also conceivable for the magnet system to be attached to the X-ray device via an attachment means allowing a reproducible attachment. Such attachment means can for example comprise at least one mechanical flange. In this way the magnet system can be removed when it is not needed. However the reproducible connection option means that as soon as it is arranged on the X-ray device again a registration between the X-ray device and the magnet system can be established again.

If the registration is to be basically established or also established before a specific process there can be provision that for registration of the magnet system and the X-ray device to the magnet system, especially to the magnet, an X-ray marker, especially a lead ball, arranged on a support marking the focus relative to the magnet is attached, in which case at least two suitable X-ray pictures of the X-ray marker are captured with the X-ray device to determine the three-dimensional position of the X-ray picture and the position of the X-ray marker is determined from the pictures, especially automatically. With this procedure a mechanical support can be attached to the magnet system reproducibly and precisely which carries an X-ray absorbing element, the X-ray marker, for example a small lead ball. The position of this small lead ball coincides with the focus of the magnetic field. With the magnets and the associated X-ray marker in position imaging is then started with the X-ray device, for example the C-arm X-ray device, whereby advantageously automatically because of the use of an X-ray marker, the pictures the position of the X-ray marker in the room can be determined from the pictures. Thus the room coordinates of the X-ray device and of the magnet system, especially the magnetic focus, can be calibrated to one another in a simple manner.

It is not always possible to determine from the image dataset alone with high accuracy the position of the target location, for example of the tumor. There can then be provision, according to the invention, for the image dataset or an image dataset derived therefrom to be fused with a previously captured three-dimensional advance dataset, especially a CT image dataset and/or a magnetic resonance image dataset and/or a PET image dataset. This consequently produces a derived image dataset to be used, especially a fusion dataset in which the position of the target location, especially of the tumor, can be determined in improved manner. The fusion in this case can be carried out using known 3D-registration methods so that a pinpoint use of these three-dimensional pre-interventional advance datasets is made possible.

Especially advantageously however there can also be provision for the advance dataset to be recorded with a magnetic resonance device at least partly registered with the X-ray device. If such registration is basically already provided, then it is especially simple to fuse the respective image datasets, here the magnetic resonance advance dataset and the captured image dataset. To realize such a registration there can especially be provision for an X-ray device and a magnetic resonance device to be used with a common z-axis, especially realized by a rail system. For example there can be provision for a patient table or patient couch to be able to be moved between the magnetic resonance device and the X-ray device, so that when the patient does not move the z-axis remains the same. In the other directions a registration can already basically be specified, even in the said direction, if corresponding fixed positions are pre-specified. Naturally it is also conceivable to carry out a registration in relation to a not yet registered axis, especially the z-axis, taking account of the data of at least one sensor, especially of an electromechanical and/or optical and/or magnetic sensor. It should be pointed out at this juncture that, in addition or as an alternative, sensors can also be provided which detect patient movements which can then also be taken into account accordingly.

Using different imaging modalities, especially a magnetic resonance device and an X-ray device, it is advantageously possible to select the corresponding recording parameters such that complementary picture data can be obtained. For example there can be provision for an advance dataset clearly showing the target location, especially the tumor, especially by use of a contrast means, to be captured as the advance dataset, tumors in particular can frequently be shown more clearly and more precisely by means of corresponding magnetic resonance images. In this context it can be expedient for the image dataset to be captured in a vessel by imaging technology highlighting the tumor, especially in a soft-tissue technology. Thus a two-dimensional or better three-dimensional representation of the relevant vessels and/or tumor areas can be created by the X-ray system, with the procedure being undertaken with and without X-ray contrast means to present the relevant anatomy. Mixed forms are of course also possible, which means that pictures are taken with and without contrast means and these are overlaid or subtracted accordingly. If for example pictures of vessels of the X-ray device are combined with tumor pictures taken by a magnetic resonance device, a fused image dataset able to be used for determining the target location is eventually obtained as an image dataset, which clearly enables the tumor and its vessels to be seen.

In a further embodiment of the present invention there can be provision for an electromagnet able to be controlled for electrically moving the focus to be used as the magnet and/or for mechanically moving the focus relative to the target location for a mechanical means of the magnet system, for example an articulated-aim robot and/or a mechanical means of a patient couch supporting a patient including the target location to be activated. A very wide variety of options is thus conceivable for achieving the relative movement of the focus in relation to the target location so that the two finally coincide. For example, for a first approximate adjustment the patient couch can initially be moved horizontally and/or vertically. Then a fine adjustment can be undertaken using mechanical means of the magnet system and/or corresponding power applied to the electromagnets of the magnet system. Especially advantageously all adjustment options are provided here which can then be used in the optimum manner to make possible a plurality of automatic and relative movements and thus ensure a precise positioning of the nanoparticles. The magnet system and the X-ray device can exchange the geometrical data of the focus and of the target location via an electronic interface for example in order to automatically carry out the positioning process.

Expediently there can also be provision for the guidance of a catheter embodied for injection of the nanoparticles, the injection and/or the positioning of the nanoparticles to be monitored by capturing at least one fluoroscopy image with the X-ray device and displaying the fluoroscopy image or a monitoring dataset derived from the fluoroscopy image, with the display especially being overlaid with the image dataset or a picture derived therefrom. The X-ray device can thus still be used for monitoring tasks, for example the fluoroscopy checking of the positioning of the catheter embodied for injection of the nanoparticles, the injection itself and/or the positioning of the nanoparticles. An overlaying with the image dataset in which the target location is or has been determined can then be useful since the target location can then be clearly seen therein and can be taken into account in the guidance, the injection or the checking of the adherence of the nanoparticles at the target location.

As already mentioned, further parameters, for example the magnet system, can be adapted within the framework of the inventive method. Thus there can be provision, as a function of planning data determined from the image dataset, for the field strength of the gradient field, especially locally, to be adapted automatically, especially by changing a voltage and/or a current of electromagnet of the magnetic resonance system. Based on calculations of a control device for example which is also responsible for positioning the focus, the field strengths of the magnet can also be adapted for example by changing voltage/current of the electromagnet.

Particularly advantageously, especially for local changes to the field strength and/or direction of the gradient field, at least one electromagnetic adaptation coil can be used. Such adaptation coils can be used in two respects: On the one hand they make possible local corrections of field strength and direction of the gradient field, which typically allows a more precise and better generation of focus. On the other hand they increase the basically available degrees of freedom in the design of the gradient field which can be adapted in accordance with the current treatment situation so that for example focuses of different embodiments can be generated for different circumstances at the target location. Thus the flexibility of the method is further increased, whereby the adaptation coils should naturally also be registered with the magnet system.

For example known techniques from the shim technology for magnetic resonance systems can be transferred to this application.

It is further advantageous for a magnetic alternating field to able to be generated at the target location by means of the magnet system and/or if necessary the adaptation coils. In this way the therapy effect of the particles can be enhanced.

Preferably an X-ray device comprising an X-ray emitter and an X-ray detector which are attached to a C-arm and/or an articulated-arm robot can be used. Such an embodiment is especially advantageous since it allows substantially better access to the patient and additional opportunities for X-ray projections. It should be pointed out that a magnet system comprising at least one articulated-arm robot can of course also be used in order to also improve the accessibility in this regard.

In an especially advantageous embodiment of the inventive method there can be provision for at least one two-dimensional or three-dimensional local image dataset to be recorded with a catheter introduced into the patient or arranged on the patient and to be fused with the image dataset or with the image dataset derived therefrom, especially the fused image dataset. In particular a catheter embodied for intravascular magnetic resonance imaging can be used for this purpose. Intravascular magnetic resonance imaging (IVMRI) is especially suitable for clearly showing the target location, especially of a tumor, and the concentrated magnetic nanoparticles. Thus further local picture information can be generated which, especially for checking the treatment, can be presented together with the image dataset or the derived image dataset, especially the fused image dataset. For example there can be provision, by the rotation of the catheter (whereby slice pictures are generated) and a simultaneous withdrawal or advance of the catheter, for three-dimensional local image datasets to be captured so that an anatomical assignment of the target location tissue and the concentrated magnetic nanoparticles is possible. It should be pointed out that with tumors very near the surface, the tip of the catheter, especially when IVMRI is used, can also be applied outside the body in order to check the concentration of the nanoparticles.

Preferably the catheter can include at least one position sensor, especially an electromagnetic position sensor and/or an ultrasound position sensor, with the data of the position sensor being taken into account for registering the image dataset with the local image dataset. Position sensors at the tip of the catheter remedy the problem of exact three-dimensional representations not being able to be achieved with known solutions. This leads to movement artifacts in the three-dimensional image processing. Preferably the position sensors are electromagnetic position sensors (EMP), for example three coils arranged at right angles to each other, with alternatives using ultrasound or suchlike also being conceivable however.

In a typical embodiment there can be provision for electromagnetic transmitters or alternatively electromagnetic receivers to be arranged in or on the catheter. In addition the corresponding electromagnetic receivers or alternatively transmitters are arranged outside the body or at a distance from it. In this case as a rule the at least one transmitter which emits in a specific spatial direction can be assigned to a receiver or conversely a receiver in a specific receiving direction of the room can be assigned to a transmitter, to make possible localization in the room. In specific cases the combination of two transmitters with one receiver or vice versa is also sufficient when the angular relationships are known and are not able to be changed. If the number of transmitters and receivers in the room is increased, the position-finding accuracy and the computing overhead increases.

As well as the method, the present invention also relates to a treatment facility for treating a target location, especially a tumor, with magnetic nanoparticles and/or microcapsules comprising nanoparticles, comprising a magnet system with at least one magnet, especially an electromagnet, for generating a magnetic gradient field guiding magnetic nanoparticles to a target location and/or keeping them there, an X-ray device registered with the magnet system or able to be registered with it, especially comprising a C-arm with an X-ray emitter and an X-ray detector arranged opposite one another thereon and a control device embodied for carrying out the inventive method.

An improved positioning of the focus of the gradient field in relation to the target location is also consequently possible by means of the inventive facility. In this case a display facility can also especially be present on which a planning diagram is shown, with an interaction with a user able to be carried out by means of a control device, for example if the position of the target location is to be determined manually and/or other planning parameters or treatment parameters are to be changed manually.

All of the embodiments with regard to the inventive method can similarly be transferred to the inventive treatment facility.

Accordingly the magnet system and/or a patient couch of the treatment facility and/or the X-ray device can preferably comprise mechanical means, especially at least one articulated-arm robot, for movement, especially displacement. These types of mechanical means can consequently be used both for adjusting the imaging geometries and also for the actual positioning of the focus of the gradient field. As already mentioned the magnet system can also comprise at least one electromagnet as its magnet, through the activation of which an electrical displacement of the focus can then also be achieved.

Advantageously the treatment facility can further comprise a magnetic resonance device, with the magnetic resonance device and the X-ray device having a common z-axis, especially implemented by a rail system. This already results in a registration in relation to at least one axis, with, as already explained in relation to the method, provision able to be made for at least one sensor, especially an electromechanical and/or optical and/or magnetic sensor, to be provided for registering the magnetic resonance device and the X-ray device in relation to further axes.

If the magnet system is not basically attached in a fixed relationship to the X-ray device, attachment means allowing a reproducible attachment for the magnetic system on the X-ray device can be provided, especially comprising mechanical flanges or the like.

Especially advantageously the magnet system can comprise at least one suitable adaptation coil for adapting the gradient field. In this way the desired four of the gradient field can be better achieved and greater freedom in its design is available.

The treatment facility can further comprise at least one catheter with an imaging device especially embodied for magnetic resonance imaging. A local image dataset can then be recorded with such a catheter which shows the target location and/or the nanoparticles particularly clearly. In this context an especially electromagnetic position determination system with at least one position sensor arranged on the catheter can also be provided. It should also be pointed out at this juncture that it is generally conceivable for the catheter provided for recording the local image dataset to be the same catheter used for the injection of the nanoparticles or of the microcapsules comprising the nanoparticles, with a plurality of capsules being administered as a rule.

Finally there can preferably be provision for at least one sensor to be provided for detecting a patient movement. Such a sensor can be used for example to avoid artifacts or the like which are caused by the patient.

Shown below are two typical workflows during the treatment of tumors, whereby only the significant steps will be described.

In a first embodiment an examination can first be undertaken with the magnetic resonance device for determining the location of the tumor in the patient. Then the body can be moved by means of a rail system to the X-ray device which is embodied as an angiography system for example. The tumor and the vessels supplying the tumor are then identified by an X-ray examination, with contrast media able to be used for example and/or soft tissue images able to be produced. The magnetic resonance advance image dataset is then fused with the image dataset recorded with the X-ray device and can be presented for example on a display facility. Now the treatment catheter is introduced into the patient, based on the fused image dataset produced. This is monitored with fluoroscopy imaging or ultrasound imaging if an appropriate ultrasound facility is provided. In such cases the pictures produced for monitoring can be shown overlaid with the fused dataset.

It is now identified where the target location, here the tumor, is to be found. For example in a planning diagram the area in which the nanoparticles are to be concentrated can be selected by a user, however automatic analyses, especially of the fused image dataset, are also conceivable. The magnet is then positioned automatically by mechanical or electrical relative displacement of the focus so that the focus matches the target location. In addition the field strength as well as the concentration of the nanoparticles is adjusted automatically. Now the nanoparticles, which are for example present as chemotherapeutic-laden microcapsules, can be injected into the blood vessels supplying the tumor.

After this has happened the patient is moved back via the rail system to the magnetic resonance device. There a magnetic resonance examination is undertaken to check whether the nanoparticles have concentrated in the intended tumor area. If it is established in this case that no sufficient concentration has been achieved, the steps, with the exception of the advanced magnetic resonance examination, can be repeated. If however a sufficient concentration is achieved, the patient can be moved away to a monitoring station.

In a second exemplary embodiment of a workflow for the treatment of tumors initially a magnetic resonance pre-examination is first carried out to determine the position of the tumor in the patient, with either a magnetic resonance device already registered with the X-ray device able to be used, but also a magnetic resonance device which does not belong to the treatment facility able to be used, in order to obtain an advance dataset in this way. In each case the patient is then transported to the X-ray device where as above the tumor and the vessels supplying the tumor are identified and a fused image dataset is determined from the image dataset recorded with the X-ray device and the advance dataset. Then the treatment catheter is once again introduced into the body, for which purpose the fused dataset can already be used, which can then be shown simultaneously with monitoring pictures, especially monitoring pictures of the X-ray device.

The steps for identification of the target location and the positioning of the focus of the gradient field ultimately execute as above, after which the typically chemotherapeutic-laden magnetic nanoparticles can be injected into the blood vessels supplying the tumor. By contrast with the first exemplary embodiment, in this case however if the treatment catheter itself does not include an imaging device embodied for intravascular magnetic resonance, a specific IVMRI catheter is introduced into the patient or, for a surface tumor, is applied extracorporeally. An IVMRI examination is now undertaken to check whether the particles have concentrated in the intended tumor area i.e. at the target location. If a sufficient concentration is not produced the preceding steps, where applicable, can be repeated again. If a sufficient concentration is achieved the patient is moved away to a monitoring station.

These examples show that the inventive method and the inventive treatment device achieve a significant improvement of the medical workflow and also a safer and more rapid concentration of the magnetic nanoparticles in the desired tumor area. This leads to a reduced patient risk and more successful therapy.

BRIEF DESCRIPTION OF THE DRAWINGS

Further advantages, features and details of the present invention emerge from the exemplary embodiments described below and also with reference to the drawing, in which.

DETAILED DESCRIPTION OF THE INVENTION

Figure 1:
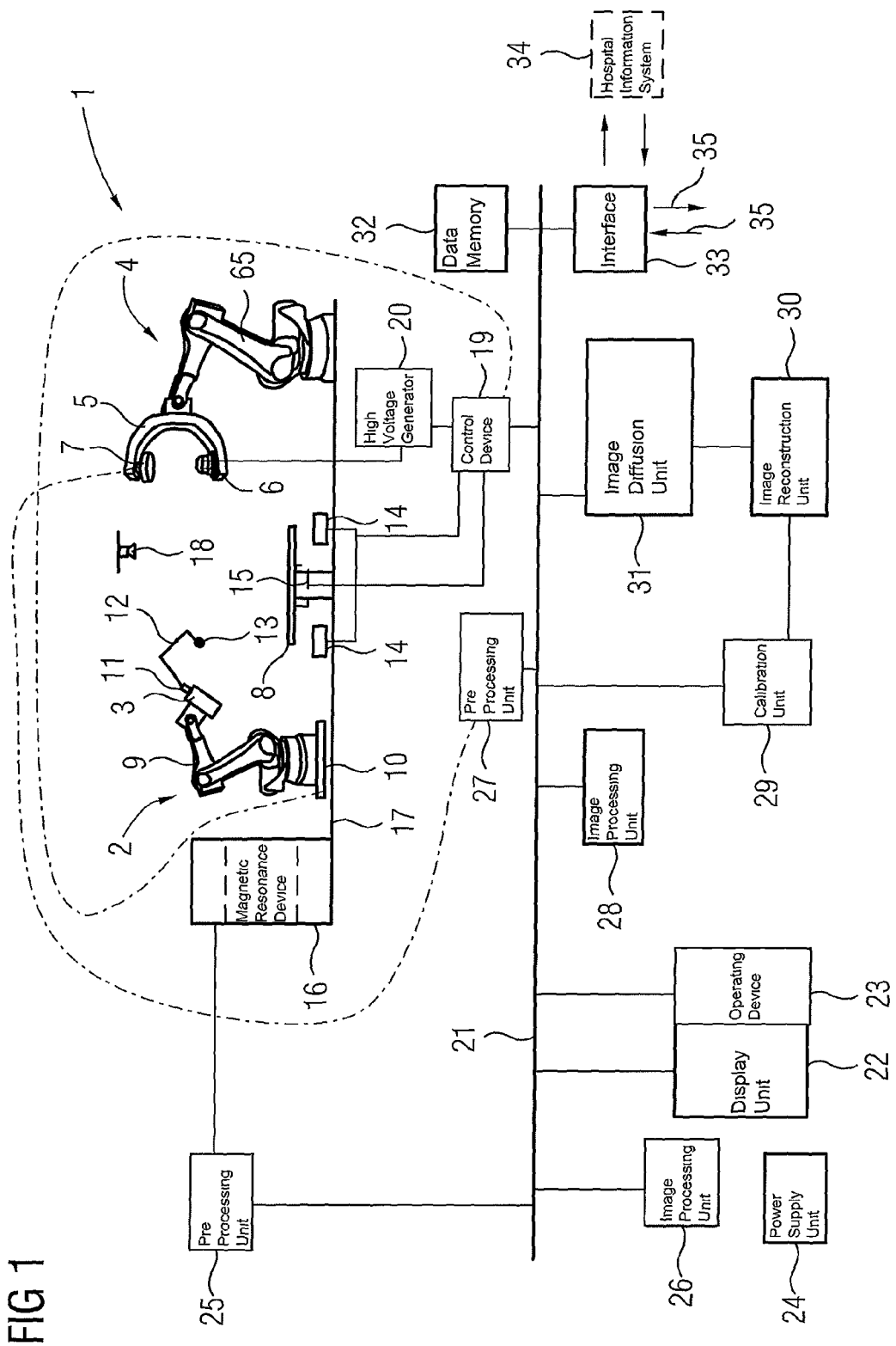
FIG. 1 shows an inventive treatment device in a first form of embodiment.

FIG. 1 shows a basic sketch of an inventive treatment facility 1. It serves, as will be described in more detail below, for tumor treatment by means of microcapsules containing magnetic nanoparticles, especially microspheres, whereby the nanoparticles are to be guided to a target location by means of a magnetic gradient field and/or are to be kept there. The gradient field is generated by a magnet system 2 with an electromagnet 3 and exhibits the greatest holding forces in an area which is referred to as the focus of the gradient field. This is where the greatest gradients are present. With the inventive treatment facility for the inventive method it is now possible to facilitate an improved positioning of the focus of the gradient field so that said field lies as precisely as possible at the target location.

To this end the treatment facility further comprises an X-ray device 4, comprising a C-arm 5 on which an X-ray emitter 6 and a flat-panel detector 7 are arranged opposite one another. The C-arm 5 itself is held by means of an articulated-arm robot 65 so that for example it can be completely removed from the treatment area on the patient couch 8. The magnet 3 too is also held on an articulated-arm robot 9.

The X-ray device 4 and the magnet system 2 are registered with one another, meaning that a transformation between their coordinate systems is known. In this case there can optionally be provision for the magnet system 2, for example if it is not needed, to be removed from the X-ray device 4, with the registration being re-established during reconnection of the magnet system 2 by specific mechanical attachment means 10, only indicated in the figure, being provided, which allows a reproducible attachment of the magnet system 2.

In addition or as an alternative, an attachment means 11 can be provided on the electromagnet 3, on which a support 12 can be arranged reproducibly in a fixed position which supports an X-ray marker 13, in this case a lead ball which for the support arranged on the magnet 3 marks the position of the focus of the gradient field for at least one setting. If at least two two-dimensional pictures of the X-ray marker 13 are now captured using the X-ray device 4, the position of the X-ray marker 13 and thus the focus in the coordinate system of the X-ray device 4 can be determined so that a registration, new if necessary, can be determined.

The treatment facility 1 also has two adaptation coils 14 with which the gradient field of the magnet system 2 can be better adapted to the current position. Techniques from the shimming area can be employed here.

The patient couch 8 is able to be adjusted in the horizontal and the vertical direction using mechanical means 15, as are fundamentally known.

Consequently, if a tumor in a patient located on the patient couch 8 is regarded as the target location, the relative position of the focus of the gradient field and of the target location can be changed in various ways. Thus on the one hand the target location can be moved, with which the mechanical means 15 is controlled accordingly. A further positioning option is represented by the articulated arm robot 9 as a mechanical means for adjusting the magnet 3. Finally the electromagnet 3 can have power applied to it in a different manner in order to achieve a sort of electrical displacement. And even the adaptation coils 14 can be used if necessary to allow a change or a displacement of the focus.

Before the method for improved positioning is discussed in practical terms it should be pointed out that the treatment facility 1 also comprises a magnetic resonance device 16, which because of the patient couch 8 guided by the rail system 17 features a shared z-axis with the X-ray device 4. A registration between the magnetic resonance device 16 and the X-ray device 4 with regards to the z-direction is achieved by electromechanical sensors not shown in any greater detail here, from which the position of the patient couch 8 can be derived precisely.

Optionally provided as further sensors can be sensors 18 which detect a movement of a patient arranged on the patient couch 8, for example optical sensors such as a camera.

For central control of the examination facility 1 a control device 19 is provided which can control the previously described systems/sensors or can receive data from the latter. In addition this is also assigned a high-voltage generator 20 for generating a high voltage for the X-ray emitter 6.

A wide variety of further components are connected via a data bus 21 to the treatment facility 1, especially a display facility 22 with an associated operating device 23. Different image datasets or pictures can be displayed on the display facility, for example a monitor, as planning datasets for example. Parameters for controlling the different systems can be entered via the operating device 23.

A power supply unit 24 is further provided to supply power to the treatment facility 1.

Images captured by the magnetic resonance device 16 are first pre-processed by a pre-processing unit 25 before they can be conveyed to an image processing unit 26 for magnetic resonance imaging. A pre-processing unit 27 and an image processing unit 28 are also provided for the X-ray images taken by the X-ray device 4. Provided as further image processing modules are a calibration unit 29 for the registrations, an image reconstruction unit 30 with a soft tissue processor and an image diffusion unit 31, with other modules for image processing naturally also able to be provided.

Images and image datasets can be stored in a picture data memory 32. Finally the treatment facility 1 includes a DICOM Interface 33 for patient data and picture data, which can exchange images for example with a hospital information system labeled 34. However image datasets, for example advance datasets, can also be conveyed from other sources to the treatment facility 1, cf. arrow 35.

Not shown in any greater detail here is the treatment catheter for injection of the nanoparticles, which can likewise be part of the treatment facility 1.

The control device 19 is now embodied for carrying out the inventive method, which means that an improved positioning of the focus of the gradient field can be undertaken with it.

To this end an advance dataset is first of all captured as a magnetic resonance imaging dataset with the magnetic resonance device 16 and this is done in a recording technology which shows the tumor particularly clearly. Then the patient is moved by the rail system 17 to the X-ray device 4. With the X-ray device 4 a number of two-dimensional X-ray images are now captured in a computed tomography-like method from different projection angles which serve, by means of the known methods, for example back projection, for reconstruction of a three-dimensional image dataset of the target region in the patient. In such cases a soft tissue technique is used here as the recording technique if necessary at least partly using a contrast medium. In such recordings the vessels supplying the tumor can be shown particularly clearly. From the image dataset which has been recorded with the X-ray device 4 a fused image dataset 36 is now determined by merging with the advance dataset of the magnetic resonance device 16 in the picture merging unit 31, which is shown by way of example in FIG. 2. The blood vessels 38 supplying the tumor 37 and also the tumor 37 itself can clearly be seen in the fused image dataset 36.

The tumor 37 as target location can be automatically determined in the fused image dataset 36 but it is also conceivable for the fused image dataset 36 to be displayed on the display facility 22 and for a user to be able to mark the area 39 as the target location using the operating device 23, in which the nanoparticles are later to concentrate.

It should be pointed out at this juncture that naturally a number of advanced datasets, if necessary also datasets captured with modalities not belonging to the treatment facility 1, can be taken into account and also fused into the fused image dataset 36.

Once the position of the tumor 37 is now known in the coordinate system of the X-ray device 4, it is also known via the registration in the coordinate system of the magnet system 2, so that the control device 19 can now generate control parameters for the different adjustment means suitable for displacing the focus of the gradient field, which lead to the focus lying precisely at the target location, i.e. the tumor 37. In such cases primarily the mechanical means 15 for horizontal and/or vertical displacement of the patient couch 8, the articulated-arm robot 9 and for electrical displacement the different application of power to the electromagnetic are to be considered as adjustment means, with smaller corrections/adaptations also able to be made via the adaptation coils 14.

Thus the focus is finally automatically positioned so that it coincides with the position of the target location.

The image dataset captured with the X-ray device 4 or the fused image dataset 36 can also be further used in other ways, in order to plan the intervention, since for example planning data can be determined automatically or manually from the image dataset, which for example describes a field strength of the gradient field suitable for the treatment, especially locally-resolved. Naturally it is also conceivable for these types of treatment parameter to be entered by a user via the operating device 23, while the planning diagram (i.e. the fused image dataset 36) is displayed on the display facility 22. Depending on such planning data the field strength of the gradient field can be adapted locally automatically by the control device, which in the present case is carried out by changing a voltage and/or a current of the electromagnet 3 of the magnet system 2. For this local change of the field strength, but also for direction adaptation, in addition or alternatively the adaptation coils 14 can also be controlled by the control device 19.

Figure 2:
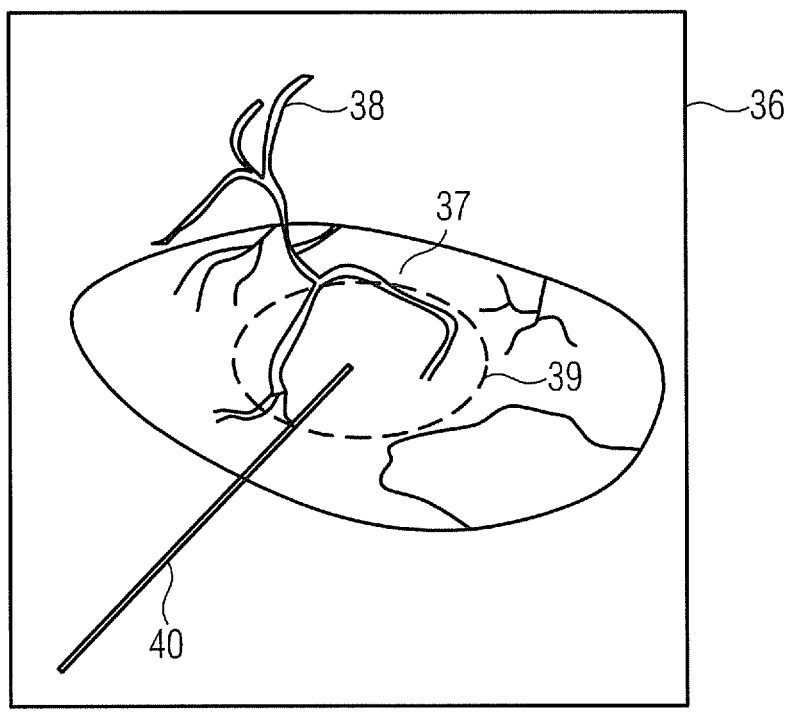
FIG. 2 shows a possible diagram for planning an intervention.

It should also be pointed out that the X-ray device 4 can also be used for monitoring the positioning of the treatment catheter for injection of the nanoparticles, by one or more fluoroscopy pictures being taken on which the treatment catheter is to be seen. These pictures can then, as is also indicated in FIG. 2, be overlaid with the fused image dataset 36 so that the treatment catheter 40 is also to be seen. The injection of the nanoparticles themselves can also be monitored, while for checking a suitable concentration of nanoparticles in the tumor 37 the patient can preferably again be moved into the magnetic resonance device 16, since the nanoparticles, because of their nature as magnetic nanoparticles, can be better recognized in a magnetic resonance image.

Finally it should be pointed out that the control device 19 can also be embodied by means of the magnet system 2 and if necessary the adaptation coils 14 to generate a magnetic alternating field at the target location, which improves the therapy effect.

Figure 3:
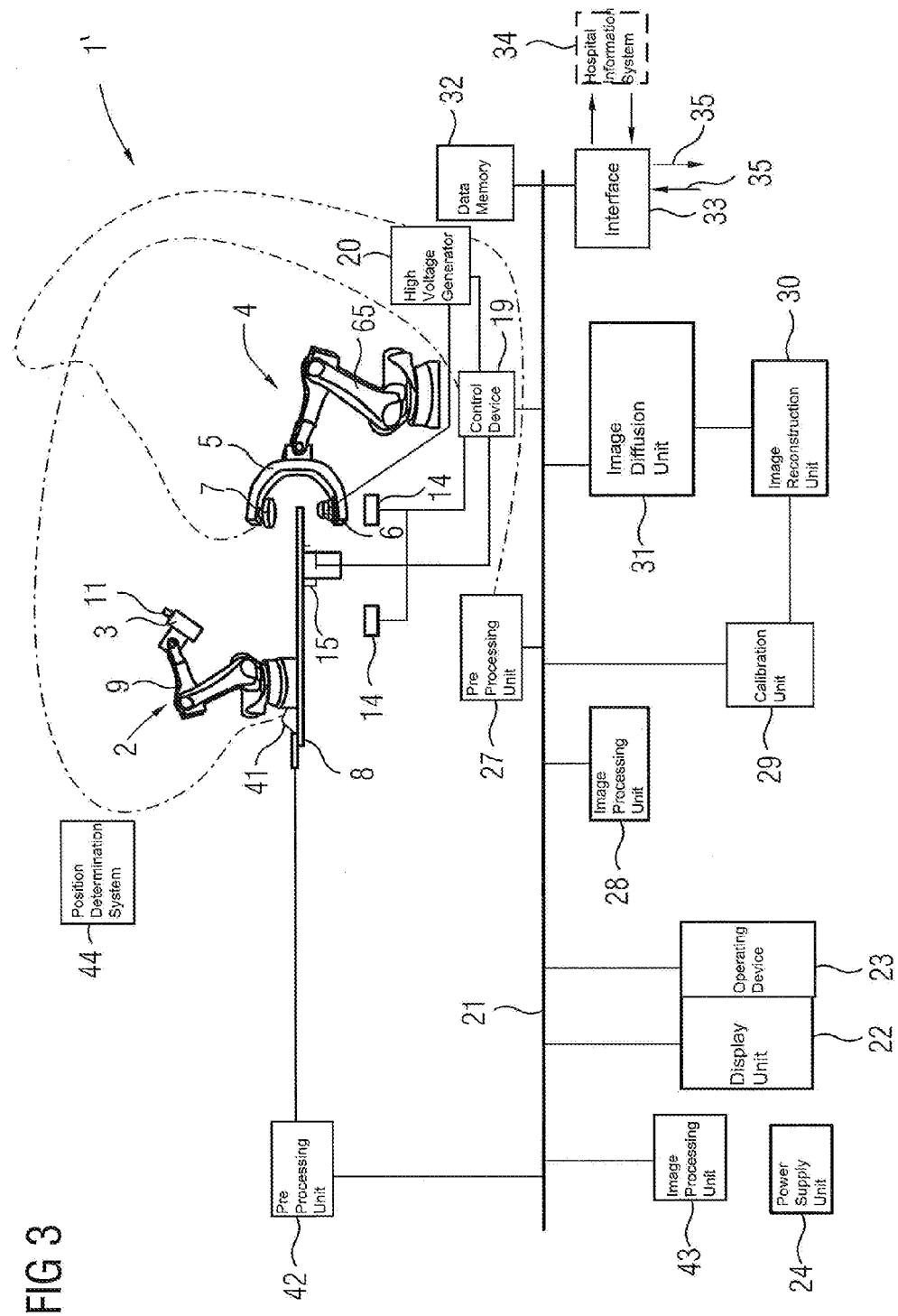
FIG. 3 shows an inventive treatment facility in a second form of embodiment.

FIG. 3 shows a further exemplary embodiment of an inventive treatment facility 1', in which, to simplify the presentation, the same components are provided with the same reference characters. It should be pointed out at this juncture that a number of optional components, for example the sensor 18, the attachment means 10, 11, the support 12 as well as the magnetic resonance device 16 and the rail system 17 are no longer shown in FIG. 3, although they can also be provided in this exemplary embodiment.

By contrast with the first exemplary embodiment the treatment facility 1' additionally comprises an IVMRI catheter 41, which is designed for intravascular magnetic resonance imaging. Accordingly this IVMRI catheter 41 is assigned a preprocessing unit 42 for the IVMRI catheter 41 and an image processing unit 43. In addition a position determination system 44 is available, which interacts with position sensors 45 arranged on the IVMRI catheter 41.

Figure 4:
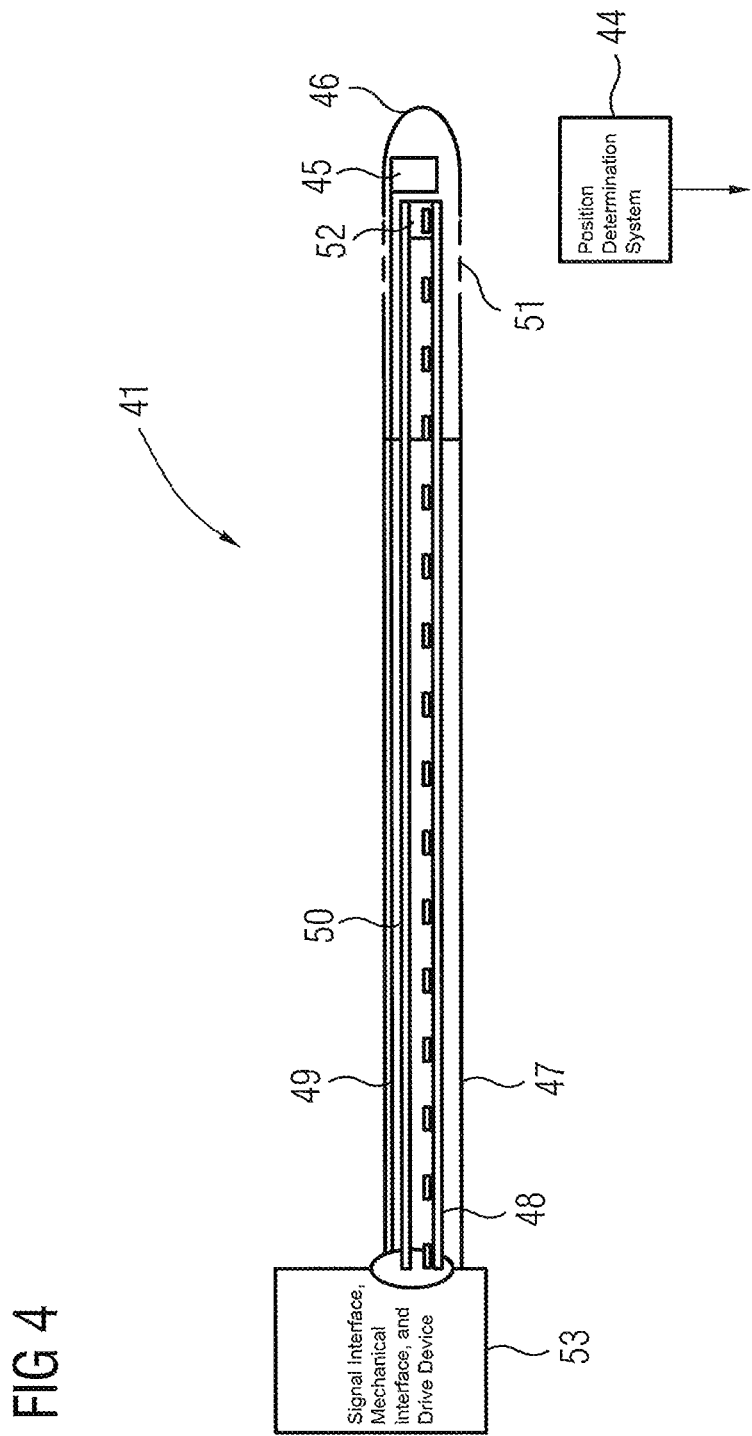
FIG. 4 shows a catheter of the treatment facility in accordance with FIG. 3.

A more precise diagram of the structure of the IVMRI catheter 41 can be found in FIG. 4. There the position sensors 45 arranged in the rounded catheter tip 46, which are arranged as electromagnetic sensors, especially coils, in the x-, y- and z-direction. In the catheter sleeve 47, which comprises a lumen 48 for the signal lines 49 to the position sensors 45 and the magnetic resonance signal lines 50, a transparent window 51 for IVMRI is provided, within which the IVMRI sensor 52 can be found. The catheter 41 is connected proximally to a device 53, which as well as a signal interface and a mechanical interface, also comprises a drive unit.

Through the use of the position determination system 44 it is possible by means of the IVMRI catheter 41 to create the most exact possible movement-artifact-free three-dimensional local image dataset. Through the rotation of the IVMRI sensor 52 slice pictures are usually created. If a simultaneous withdrawal or advance of the IMRI catheter 41 now takes place, three-dimensional images are created, whereby to determine a corresponding local image dataset the data of the position determination system 44 is also taken into account.

Figure 5:
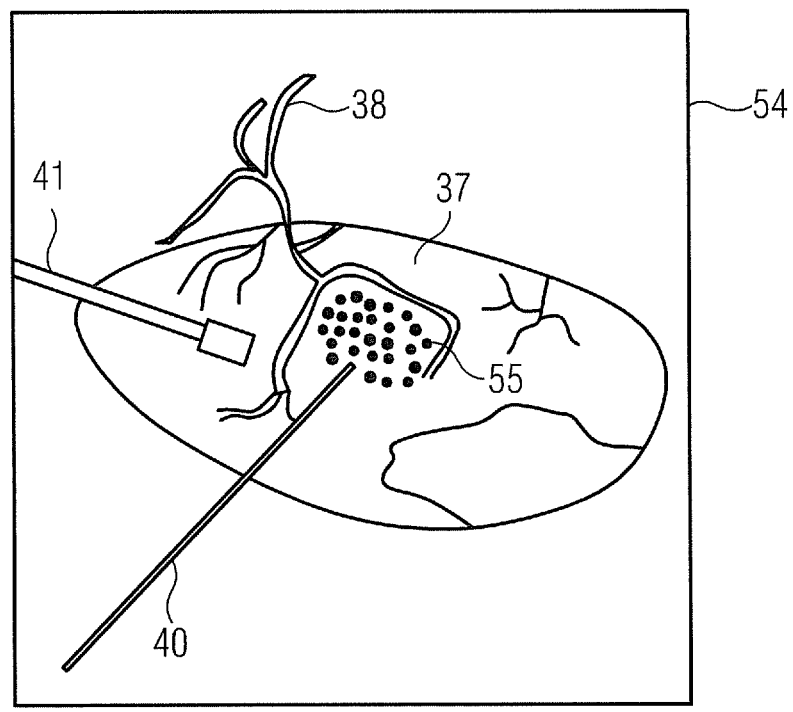
FIG. 5 shows a display in the process of tumor treatment.

In the treatment of tumors the IVMRI catheter 41 provides an advantageous option for checking the concentration of the nanoparticles in the tumor. To do this, after injection of the nanoparticles, the IVMRI catheter 41 is guided to the tumor 37 if necessary using fluoroscopy monitoring, as is shown in the example diagram 54 in FIG. 5. This diagram again shows the supply vessels 38 of the tumor 37 and also, indicated in the middle of the diagram, the concentrated nanoparticles 55. The diagram also shows the treatment catheter 40 as well as the IVMRI catheter 41.

If the IVMRI catheter 41 is guided close to the tumor 37, which with surface tumors 37 can also occur on the surface of the patient, the local image dataset can be recorded in which both the tumor 37 and also the nanoparticles 55 can be clearly seen. It can thus be decided whether the concentration in the tumor 37 is sufficient for its treatment or whether a further injection must be carried out.

It should be pointed out that it is naturally also conceivable to realize the catheters 40 and 41 in a single catheter so that one catheter fewer is needed.

Figure 6:
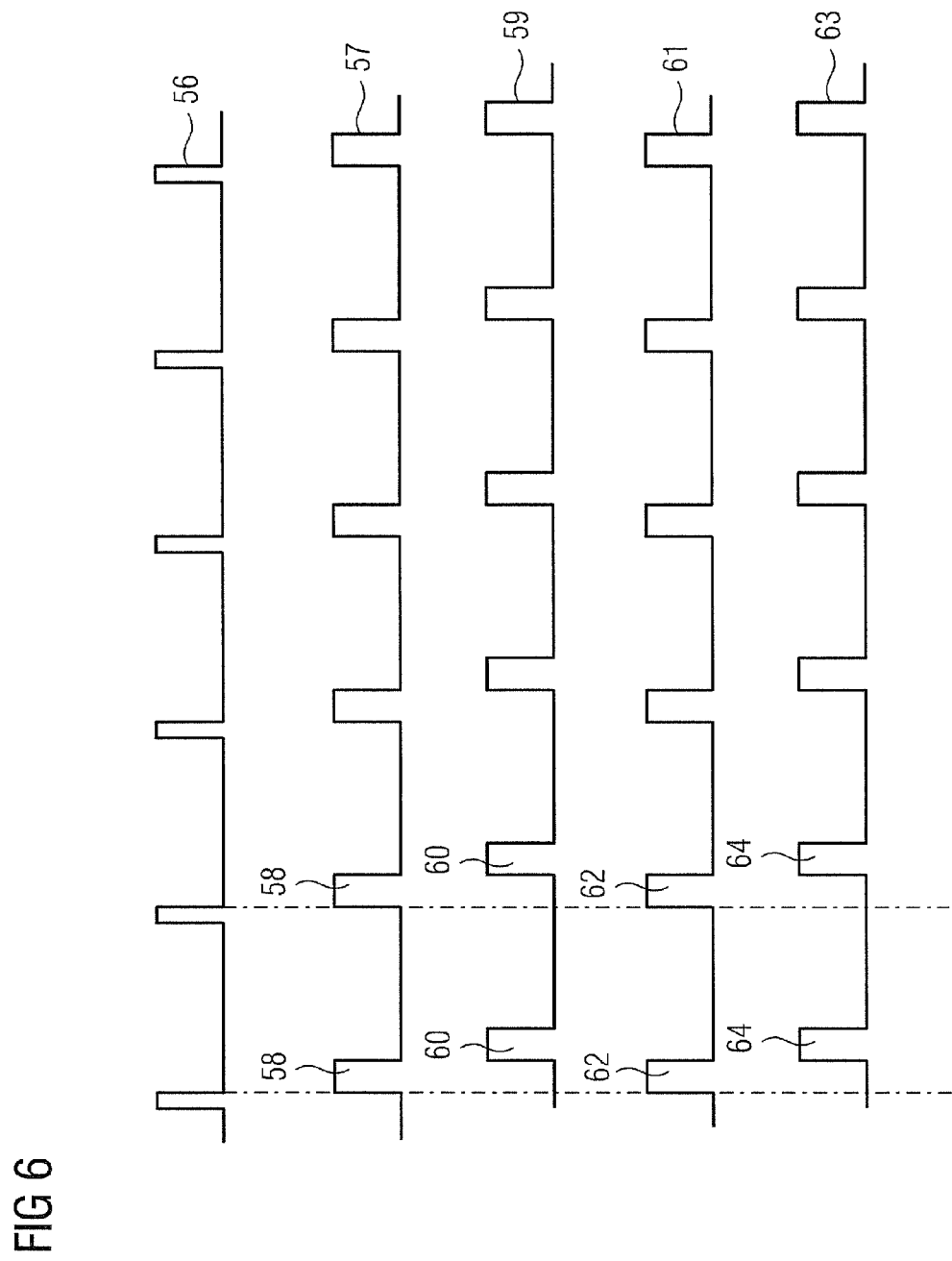
FIG. 6 shows a graphical representation for temporal displacement and timed reading out of different sensors.

Since operation is with IVMRI, with an electromagnetic position determination and the magnet system 2, a precisely synchronized readout is necessary which means that the corresponding sensors 45, 52 are read out offset in time and clocked, as can be seen in greater detail in FIG. 6. The graph 56 is shown in this diagram to illustrate the system clock. The graph 57 indicates time segments 58 in which the X-ray emitter is operated, while graph 59 shows time segments 60 in which the X-ray detector 7 is read out, the magnetic positioning is active in the segments 62 shown by graph 61, while IVMRI data is recorded in the time segments 64 shown by the graph 63, which of course do not overlap with the time segments 62.

Thus, as shown, not only an improved positioning of the gradient field is possible with the treatment facility 1 or 1' but also the concentration of the nanoparticles at the target location can be checked in an improved manner. The treatment facilities which create a useful hybrid system by registration of different components thus simplify the medical workflow significantly.

The invention claimed is:

1. A treatment device for treating a target location with magnetic nanoparticles, comprising:
   a magnet system comprising a magnet for generating a magnetic gradient field;
   an X-ray device for capturing a three-dimensional image dataset showing the target location, the X-ray device comprising a C-arm with an X-ray emitter and an X-ray detector arranged opposite one another thereon;
   a control device for:
      determining a position of a focus of the magnetic gradient field from a magnetic field map of the magnet being stored in the control device;
      registering the X-ray device with the magnet system;
      generating control parameters for positioning the position of the focus of the magnet gradient field relative to the target position so that the position of the focus coincides with the target location based on the registration;

a treatment catheter for injecting the magnetic nanoparticles to the target location being guided by the magnetic gradient field;

a patient couch for supporting a patient;

a rail system that moves the patient couch between the magnet system and the X-ray device having a common z-axis;

a mechanical device that is activated for initially adjusting the position of the focus of the magnet gradient field relative to the target position by horizontally and/or vertically displacing the patient couch based on the control parameters; and an articulated-arm robot holding the magnet that is activated for finely adjusting the position of the focus of the magnet gradient field relative to the target position by displacing the magnet based on the control parameters, wherein the registration between the X-ray device and the magnet system is carried out in the common z-axis.

2. The treatment device as claimed in claim 1, wherein an X-ray marker for marking the focus relative to the magnet is arranged on a support, wherein the X-ray marker is a lead ball attached to the magnet system, wherein at least two X-ray images are captured by the X-ray device, and wherein a three-dimensional position of the X-ray marker is determined from the two X-ray images.

3. The treatment device as claimed in claim 1, wherein the magnet system is attached to the X-ray device via an attachment device allowing a reproducible attachment.

4. The treatment device as claimed in claim 1, wherein the magnet is an electromagnet for electrically displacing the focus relative to the target location based on the control parameters.

5. The treatment device as claimed in claim 1, further comprising an electromagnetic adaptation coil for locally modifying field strength and/or direction of the gradient field.

6. The treatment device as claimed in claim 1, wherein the C-arm is attached to another articulated-arm robot.

7. The treatment device as claimed in claim 1, wherein a two-dimensional local image dataset or a three-dimensional local image dataset having a catheter introduced into a patient or arranged on the patient is captured and is fused with the image dataset.

8. The treatment device as claimed in claim 7, wherein the catheter is an intravascular magnetic resonance imaging catheter.

9. The treatment device as claimed in claim 7, wherein the catheter comprises a position sensor, wherein the position sensor is an electromagnetic position sensor and/or an ultrasound position sensor, and wherein the image dataset is registered with the local image dataset based on data of the position sensor.

10. A method for treating a target location with magnetic nanoparticles being guided by a magnetic gradient field, the magnetic gradient field being generated by a magnet of a magnetic system, comprising:

capturing a three-dimensional image dataset showing the target location by an X-ray device, the X-ray device comprising a C-arm with an X-ray emitter and an X-ray detector arranged opposite one another thereon;

determining a position of a focus of the magnetic gradient field by a control device;

registering the X-ray device with the magnet system;

generating control parameters by the control device for positioning the position of the focus of the magnet gradient field relative to the target position so that the position of the focus coincides with the target location based on the registration; and injecting the magnetic nanoparticles to the target location being guided by the magnetic gradient field by a treatment catheter;

initially adjusting the position of the focus of the magnet gradient field relative to the target position by horizontally and/or vertically displacing a patient couch based on the control parameters; and finely adjusting the position of the focus of the magnet gradient field relative to the target position by displacing the magnetic system based on the control parameters, wherein the X-ray device and the magnet system comprises a common z-axis implemented by a rail system moving the patient couch between the X-ray device and the magnet system, and wherein the registration between the X-ray device and the magnet system is carried out in the common z-axis.

11. The method as claimed in claim 10, wherein the image dataset is fused with a previously captured three-dimensional dataset, and wherein the previously captured three-dimensional dataset is a CT image dataset and/or a magnetic resonance image dataset and/or a PET image dataset.

12. The method as claimed in claim 11, wherein the previously captured three-dimensional dataset is captured by a magnetic resonance device that is at least partly registered with the X-ray device.

13. The method as claimed in claim 12, wherein the registration is carried out in the common z-axis based on a position of the patient couch and/or a movement of the patient.

14. The method as claimed in claim 10, wherein the injection and/or positioning of the nanoparticles is monitored by a fluoroscopy image captured with the X-ray device, wherein the fluoroscopy image or a monitoring dataset derived from the fluoroscopy image is displayed, and wherein the display is overlaid with the image dataset or with a further image dataset derived from the image dataset.

15. The method as claimed in claim 10, wherein a field strength of the magnetic gradient field is adapted automatically as a function of data determined from the image dataset, and wherein the adaptation is performed by changing a voltage and/or a current of an electromagnet of the magnet system.

16. The method as claimed in claim 10, wherein the magnetic nanoparticles are held at the target location.

17. The method as claimed in claim 10, wherein a further image dataset is determined from the captured image dataset and the position of the target location is determined in the further image dataset.

18. The method as claimed in claim 10, wherein the magnetic system is finely adjusted by mechanically displacing the magnet.

19. The method as claimed in claim 10, wherein the magnetic system comprises an electromagnet and is finely adjusted by applying different power to the electromagnet.

* * * * *